United States Patent
Chhit et al.

(10) Patent No.: US 10,646,212 B2
(45) Date of Patent: May 12, 2020

(54) DEVICES AND METHOD FOR ACCESS AND VISUALIZATION FOR LUMBAR INTERBODY FUSION (LIF)

(71) Applicant: Rebound Therapeutics Corporation, Irvine, CA (US)

(72) Inventors: Ravut Chhit, Irvine, CA (US); Peter G. Davis, Irvine, CA (US); Ross Tsukashima, Irvine, CA (US); Todd D. McIntyre, Irvine, CA (US); Jeffrey J. Valko, Irvine, CA (US); Michael R. Henson, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 0 days.

(21) Appl. No.: 16/262,543

(22) Filed: Jan. 30, 2019

(65) Prior Publication Data
US 2019/0307439 A1 Oct. 10, 2019

Related U.S. Application Data

(60) Provisional application No. 62/795,845, filed on Jan. 23, 2019, provisional application No. 62/624,021, filed on Jan. 30, 2018.

(51) Int. Cl.
*A61B 17/02* (2006.01)
*A61B 1/32* (2006.01)
*A61B 90/00* (2016.01)

(52) U.S. Cl.
CPC ............ *A61B 17/0206* (2013.01); *A61B 1/32* (2013.01); *A61B 17/0218* (2013.01); *A61B 90/361* (2016.02); *A61B 2017/0256* (2013.01)

(58) Field of Classification Search
CPC . A61B 17/0206; A61B 17/02; A61B 17/0218; A61B 2017/0256
See application file for complete search history.

(56) References Cited

U.S. PATENT DOCUMENTS

| | | | |
|---|---|---|---|
| 2008/0300465 A1 | 12/2008 | Feigenwinter | |
| 2010/0312069 A1 | 12/2010 | Sutherland et al. | |
| 2014/0005484 A1* | 1/2014 | Charles | A61B 17/02 600/201 |
| 2014/0179998 A1 | 6/2014 | Pacey et al. | |

FOREIGN PATENT DOCUMENTS

WO WO2013116489 8/2013

OTHER PUBLICATIONS

International Search Report and Written Opinion dated May 20, 2019 from IA No. PCT/US2019/015857.

* cited by examiner

*Primary Examiner* — Julianna N Harvey
(74) *Attorney, Agent, or Firm* — Crockett & Crockett, PC; K. David Crockett, Esq.

(57) ABSTRACT

A camera and expandable bladed retractor system. The system includes a camera, with a distal-most optical element disposed over the proximal end of the lumen or surgical channel established by the retractor blades. The camera may be fixed to the retractor, either to the proximal end of a blade or to a frame member.

2 Claims, 7 Drawing Sheets

DEVICES AND METHOD FOR ACCESS AND VISUALIZATION FOR LUMBAR INTERBODY FUSION (LIF)

This application claims priority to U.S. Provisional Application 62/624,021, filed Jan. 30, 2018, and U.S. Provisional Application 62/795,845, filed Jan. 23, 2019.

FIELD OF THE INVENTIONS

The inventions described below relate to the field of spine surgery.

BACKGROUND

Various conditions of the spine, such as herniated discs, arthritis (spondylosis), misalignment of the spine (spondylolisthesis, scoliosis or hyperlordosis/kyphosis) can be treated with minimally invasive surgery, which is accomplished through narrow channels created and maintained by expandable bladed retractors. For example, Lumbar Interbody Fusion surgery is used to fuse adjacent vertebra, to treat a variety of conditions. The surgery entails removal of a portion of an intervertebral disc, placement of a "cage" or "interbody fusion device" between the discs, and placement of bone graft material between the discs (and subsequent installation of screws and posts to hold the two vertebrae in place while they fuse together). To gain access to the intervertebral disc in a minimally invasive surgery, a surgeon may approach the spine through a retractor system placed in one of several pathways. The spine may be approached from the side of the patient (lateral lumbar interbody fusion), from the front of the patient (anterior lumbar interbody fusion), obliquely from the front of patient (oblique lumbar interbody fusion), from the back of the patient (posterior or transforamen lumbar interbody fusion), and obliquely from the back of the patient (oblique lateral interbody fusion). Especially for the deeper routes (anterior, oblique, and lateral routes), a retractor system with long retractor blades is used, and visualization is currently obtained through a surgical loop or a surgical microscope intermittently looking down the passage. These instruments are necessarily disposed quite a distance from the surgical opening, making it difficult to view the surgical space, and require a surgeon to look through the loop or microscope, which may require taking on an uncomfortable posture while performing surgery. Visualization through an endoscope has also been proposed, with the endoscope disposed within the channel established by the retractor blades and extending to the distal end of the blades, near the surgical field. The endoscope takes up valuable space within the channel, and does not provide a view of tool tips within the channel, and the field of view may be limited if the endoscope is placed close to the surgical field.

SUMMARY

The devices and methods described below provide for improved lateral surgical access and visualization for minimally invasive lumbar interbody fusion procedures, to treat conditions of the spine such as herniated discs, arthritis (spondylosis), misalignment of the spine (spondylolisthesis, scoliosis or hyperlordosis/kyphosis). The devices comprise bladed retractors which include two or more blades which are separable to retract tissue overlying the spine, and a camera disposed at the proximal end of the retractor. The device can further comprise an optical assembly including a lens and a prism, disposed on one of the retractor blades, which may be moved along the length of the blade, to obtain a view of a surgical site deep within the body, or an optical assembly including a lens and a prism, disposed on one of the retractor blades, which may be tilted over the opening of the retractor, to obtain a view of a surgical site deep within the body. The camera assembly may also be mounted on a camera boom, attachable to the retractor system, which allows for translation of the camera on 2 or 3 axes relative to the retractor frame or surgical opening, and/or allows for rotation of the camera to align the camera viewing axis with the surgical workspace at the distal end of the retractor blades. With these features, a surgeon can obtain images of a surgical field deep within the body, through a surgical channel maintained by retractor blades of variable configuration, and alter the viewing axis of the camera as necessary to account for expansion of the bladed retractor.

DETAILED DESCRIPTION OF THE INVENTIONS

Figure 1:
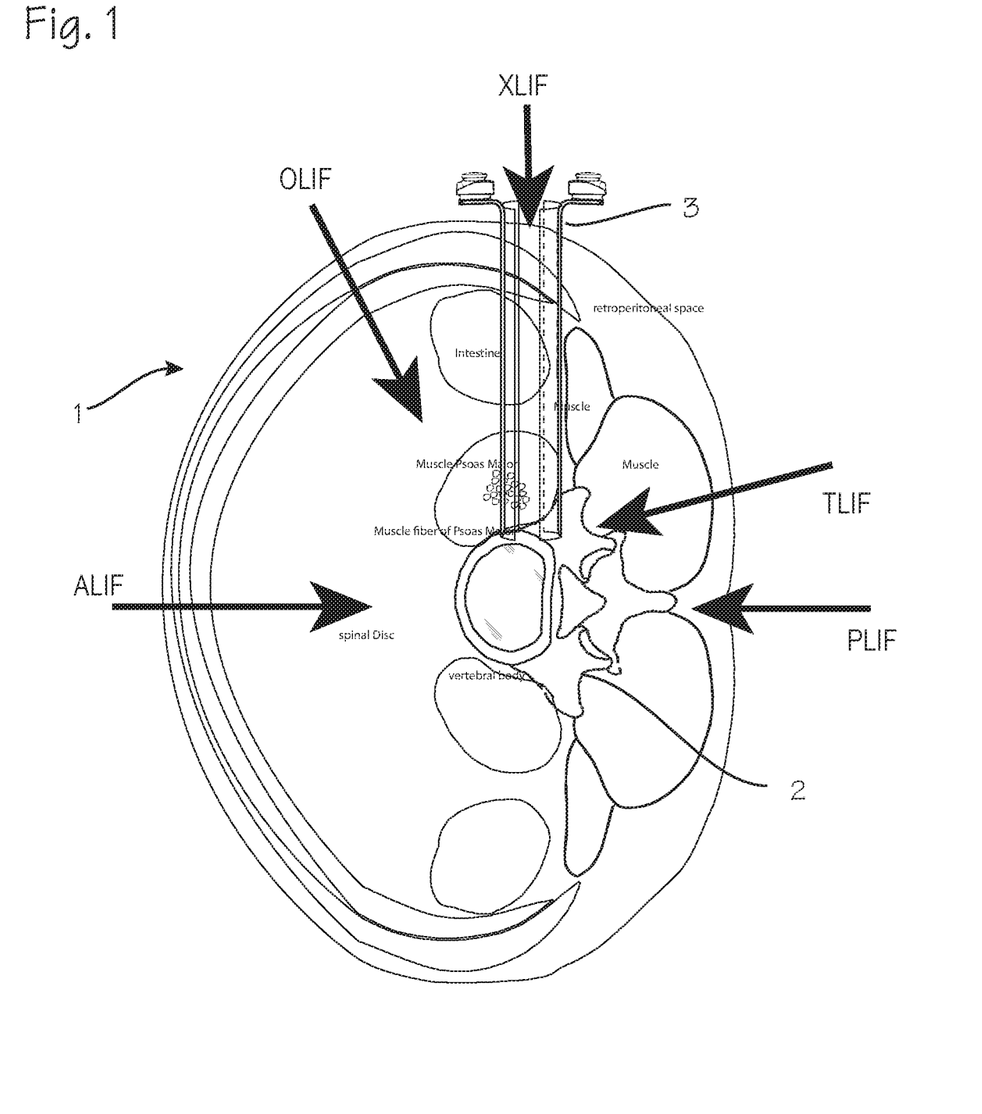
FIG. 1 illustrates typical surgical approaches to the spine, for which the retractor may be used.

FIG. 1 illustrates typical surgical approaches to the spine, for which the retractor may be used. This illustration shows a coronal cross section of a patient 1, taken through the midsection at the level of the lower back and lumbar spine. Lumbar Interbody Fusion surgery is used to fuse one vertebra, such as vertebra 2, to an adjacent vertebra, to treat a variety of conditions. The surgery entails removal of a portion of an intervertebral disc, placement of a "cage" or "interbody fusion device" between the discs, and placement of bone graft material between the discs (and subsequent installation of screws and posts to hold the two vertebrae in place while they fuse together). To gain access to the intervertebral disc in a minimally invasive surgery, a surgeon may approach the spine through a retractor system 3 placed in one of several pathways. As shown in FIG. 1, the spine may be approached from the side of the patient (lateral lumbar interbody fusion), from the front of the patient (anterior lumbar interbody fusion), obliquely from the front of patient (oblique lumbar interbody fusion), from the back of the patient (posterior or transforamen lumbar interbody fusion), and obliquely from the back of the patient (oblique lateral interbody fusion). Especially for the deeper routes (anterior, oblique, and lateral routes), a retractor system with long retractor blades is used, and visualization, which is currently obtained through a surgical loop or a surgical microscope intermittently looking down the passage, may instead be obtained with a camera assembly with optical components mounted to one of the retractor blades or retractor frame arms. Images obtained by the camera can be displayed on a display screen viewable by the surgeon, and the surgeon can perform procedures through the retractor while viewing the procedure on the display. (This system may use multiple camera assemblies, including a separate camera assembly on each blade.)

Figure 2:
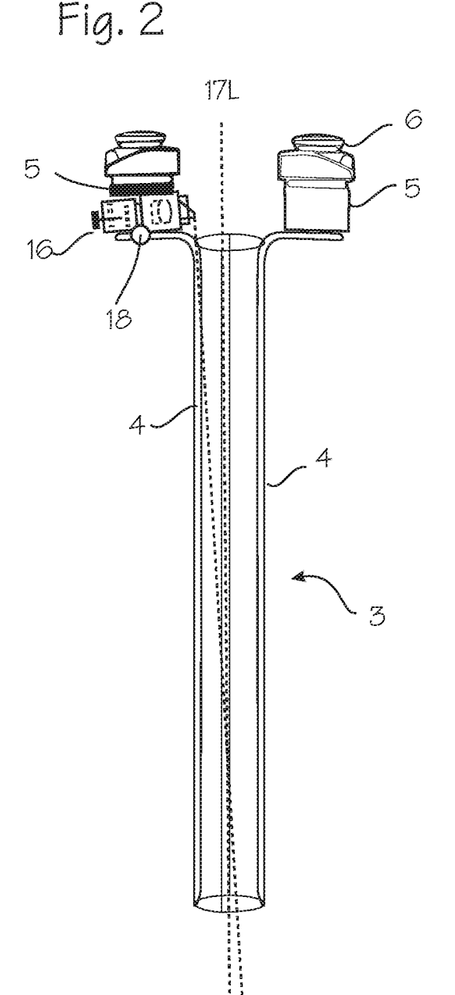
FIGS. 2, 3 and 4 illustrates a bladed retractor system suitable for access to the lumbar spine, fitted with optical elements and a proximally mounted camera.
Figure 3:
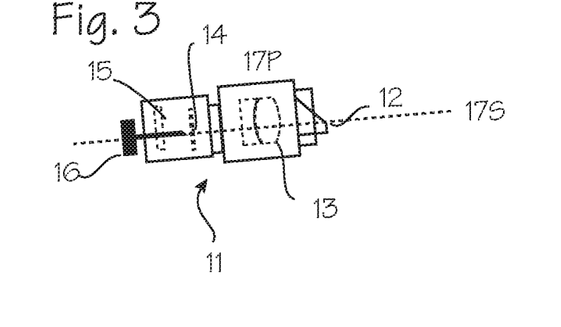
Figure 4:
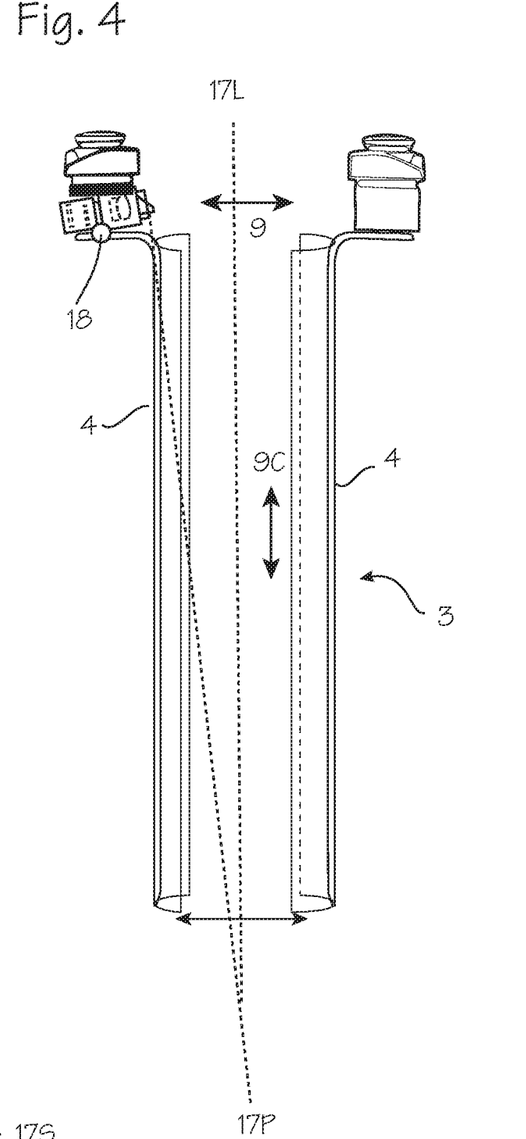
Figure 5:
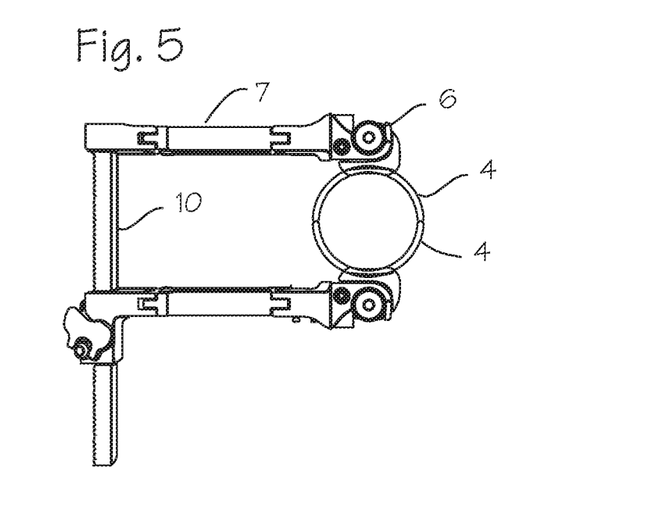
FIGS. 5 and 6 are proximal views of the bladed retractors system of FIGS. 2 and 4.
Figure 6:
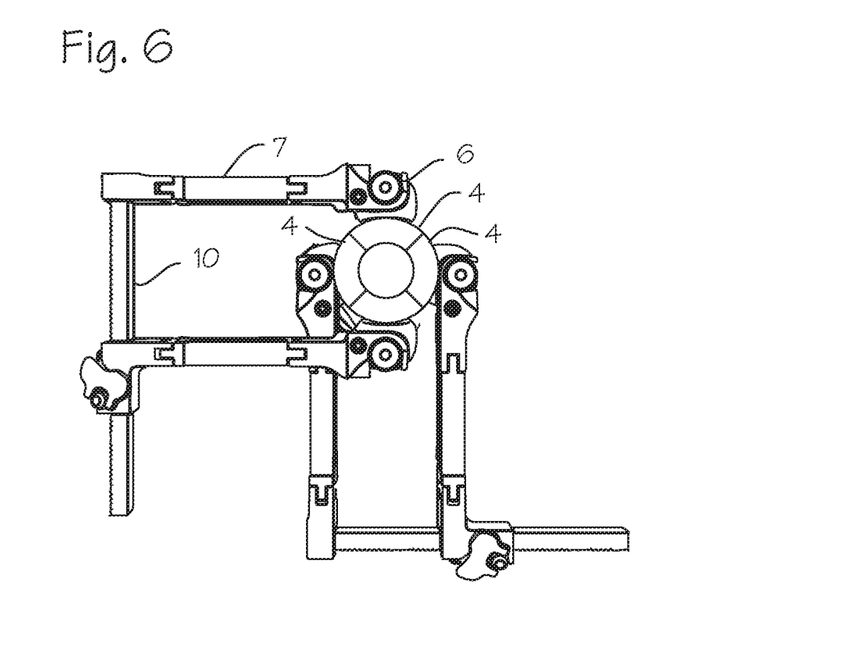
Figure 7:
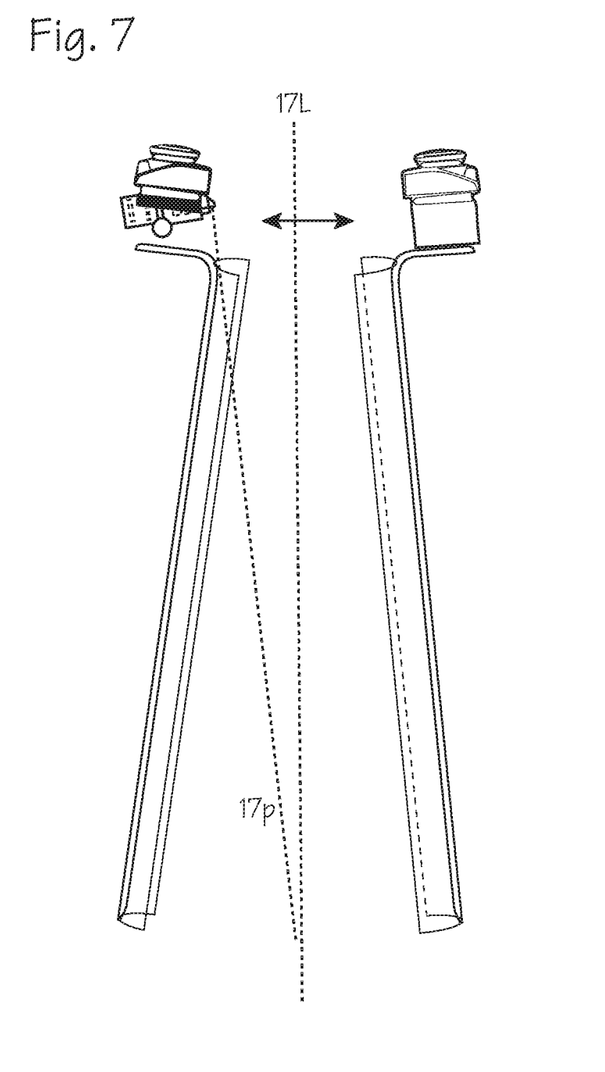
FIG. 7 illustrates a retractor system with splayed blades, with a camera rotatably mounted on the proximal end of a blade.
Figure 10:
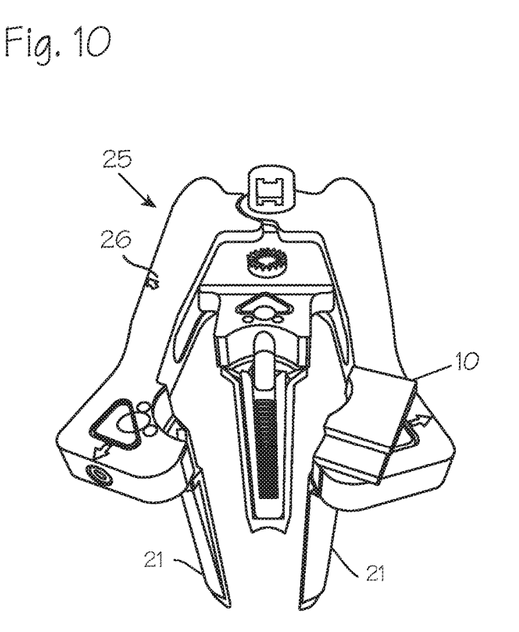

As shown in FIGS. 2 through 7, the system includes the retractor 3 comprised of several blades 4 depending from a frame 5. Fixation elements 6 (manually operable screws, clamps, or any other manually operable means for fixation) at the proximal end of each blade are interoperable with the arms 7 of the frame. The frame holds the blades in rigid but adjustable relationship to each other and the frame opening 8, over a surgical opening 9 in the patient, to maintain a surgical channel 9C between the blades, providing access to the surgical workspace at or beyond the distal end of the retractor blades. The blades may be provided in many forms. As shown in FIGS. 2 and 4, the blades are half-pipes which, when positioned together make up a complete tube, and, when separated, comprise two opposing half-pipes defining and bounding the surgical opening 9 which is the open space suitable for insertion of tools between the retractor blades to reach tissue at the distal end of the retractor blades (i.e., a surgical corridor). The blades may be flat and straight, or flared, instead of the partial pipes shown. The frame may be provided in many forms. The form in FIG. 5 is common, and includes one or more ratcheted frame members 10 and corresponding frame arms 7, with blades 4 fixed to the blade arms. The frame arms may be moved incrementally along the ratcheted frame members to move the blades toward or away from each other to retract body tissue outside the blades, and the blades may be movable along the frame arms to adjust the distance between the blades and the ratcheted frame member. FIG. 4 shows the retractor of FIG. 2 with the blade separated, space along the frame (the frame is shown in FIG. 5). Various configurations of bladed retractors are in use, with various structures for adjusting the spacing of the blades. For example, the frame can comprise a plier-style tool, with jaws set on hinges, as in a TIMBERLINE® retractor or MAXACESS® retractor, where the jaws are equivalent to the arms of a framed retractor, or the frame comprises a system with arms that slide along straight or curved frame members, such as the Braun MIASPAS® retractor, the Globus Medical Mars retractor, or the Medtronic DLIF retractor. The split tube (pair of half pipes) makes up the retractor shown in FIGS. 2 and 4, but any number of blades may be used to make up the split tube. As shown in FIG. 6, a retractor system can include a tube retractor with four quarter-pipe segments. (And, as shown in FIG. 10, a retractor system can include a tube retractor with three blades.)

As shown in FIGS. 2 and 4, a camera assembly (a camera, or the image sensing and optical components of a camera), are disposed on the proximal end of one of the blades (or on the frame). The camera 11, shown in more detail in FIG. 3, comprises the prism or reflector (or set of mirrors) 12, a lens or lenses 13 (which may include an achromatic lens or other doublet), the imaging device 14 and the control system 15 (if provided in the camera component of the system). The camera assembly may also include a focal length adjustment knob 16 for translating the imaging sensor along the primary imaging axis, relative to the housing. The lens 13 may be part of an optical assembly that includes additional optical components (filters, beam splitters, etc.). The imaging device 14 may be any suitable image sensor such as a CCD sensor or CMOS sensor. The control system 15 may include a controller, data processing components and transmitters such as a controller and a transmitter and appropriate image processing software to control the camera and transmit data from the camera (the data output system may be located off the device). Suitable cables or wireless transmitters may be used to connect the camera to a display system and a power supply. The imaging sensor is characterized by an imaging plane, and the prism is aligned with the imaging plane to direct light directed parallel to the imaging plane toward the imaging plane. As illustrated, the imaging plane is parallel to the long axis of the assembled blades, and the prism/reflector is disposed along a line perpendicular to the imaging plane, and is oriented to direct light from the surgical field at the distal end of the cannula tube onto the imaging plane.

In the system of FIGS. 2 and 4, all the components of the camera assembly are disposed proximate the proximal end of the retractor blades, with the distal-most optical component of the camera assembly (such as the distal face of the prism or the distal surface of an objective lens) proximate the proximal end of the retractor blades, and preferably proximal to the proximal end of the retractor blades (and, preferably, outside the body of the patient), so that the entirety of the camera assembly is located outside the lumen established by the retractor blades and bounded by the distal and proximal ends of the retractor blades.

The arranged retractor blades define the surgical channel and a longitudinal axis 17L which extends through the space defined and bounded by the blades. The imaging sensor has an imaging sensor viewing axis (a primary viewing axis) 17S, extending at a perpendicular to the sensor surface and intersecting a radially facing surface of the prism. As illustrated, the central longitudinal axis and the imaging sensor viewing axis intersect at about an 85-95° angle. In alternative configurations, the angle is within the range of about 45° to 135°, or within the range of about 60° to 120°. The angle may be greater than or less than 90° depending upon the desired configuration and the distance between the retractor blades when separated during use.

The prism is characterized by a prism viewing axis 17P (a secondary viewing axis, which is the line of sight through the cannula, from the prism to the distal end of the cannula) which intersects a distal surface of the prism, and extends axially distally through the tubular body toward target tissue. The prism viewing axis preferably intersects a longitudinal axis of the blade assembly (a central axis, for symmetrical blade arrangements, or a near central axis for other configurations) near the distal end of the blades, or within about 4 cm or 2 cm or less from the distal end of the cannula. The prism overhangs the retractor opening by no more than about 25% of the inside diameter of the lumen, generally by no more than about 15% or 10% or less of the inside diameter of the retractor opening (when the blades are closed together as shown in FIG. 2), such that it minimally interferes with instruments passing through the retractor opening. Thus, the prism viewing axis 17P preferably resides at an angle to the central longitudinal axis. Depending on the type of prism used, the prism viewing angle may be perpendicular to the distal optical surface of the prism (for a reflective, right angle prism shown in the figures, in which the long surface is used as the roof, for example), and the prism may be disposed over the retractor opening such that the distal optical surface is tilted slightly, relative to the transverse plane of the retractor opening, to aim the prism viewing axis at the desired point, such as an intersection with the central longitudinal axis of the retractor opening at the distal end of the cannula. For other reflective and deflective prisms for which the viewing angle is not perpendicular to the distal optical surface, the distal optical surface can be angled, as appropriate, to aim the prism viewing axis at the desired point such as an intersection with the central longitudinal axis of the cannula at the distal end of the cannula. Various forms of prisms may be used, including a pentaprism, half pentaprism (a non-inverting and non-reverting prism which bends light 45° from the prism viewing axis, so that the imaging sensor viewing axis may be disposed at about a 45° angle to the prism viewing axis or the cannula longitudinal axis), a Schmidt prism (an inverting and reverting prism which bends light 45° from the prism viewing axis, so that the imaging sensor viewing axis may be disposed at about a 45° angle to the prism viewing axis or the central longitudinal axis), Porro prisms (an inverting and reverting prism which displaces the light entering the prism to an offset but parallel path, so that the imaging sensor viewing axis may be parallel to but radially displaced from to the prism viewing axis or the central longitudinal axis) or other prisms, or combinations or configurations of prisms (and Amici/Penta prism combination, for example, or a right angle prism disposed with the long surface facing distally, so that the right angle surfaces serve the reflecting surfaces to redirect the image along an anti-parallel path to the prism viewing axis, optionally paired with a second right angle prism to redirect the image to a parallel but offset path, or a Bauerfeind prism), operable to reflect or displace light from the distal end of the cannula toward the imaging sensor.

The central longitudinal axis of the system is variable, depending on how far apart the blades are positioned. The camera is thus hinged to the retractor system, either to the frame or to the proximal end of a blade, such that it is rotatable about an axis perpendicular to a long axis of the surgical channel. The camera may be secured to the system through a hinge, a crescent hinge, a flex hinge or rocker 18, so that the camera may be tilted to direct the prism viewing axis to the center of the surgical field distal to the blades (or elsewhere in the surgical field). The camera may be tilted manually by the surgeon, or it may be tilted in response to opening of the retractor blades, through linkages connecting the camera and hinged to the retractor frame members and the retractor arms. Also, the retractor system may be capable of splaying the blades, so that the distal tips of the blades are farther apart than the proximal end of the blade. This is depicted FIG. 7. With the camera assembly rotatably mounted on the frame or blade, the camera may be rotated to keep the prism viewing axis directed toward the desired point in the surgical space. This will typically be a point at or near an intersection of the central longitudinal axis at or near the distal end of the blades, or just distal to the distal end of the blades. The rotation of the camera may be accomplished through mechanical linkages to the frame and blade, or it may be accomplished manually by the surgeon using the retractor. The rotation may be accomplished gradually as the retractor blades move from a closed configuration to an open configuration and vice-versa, or it may be accomplished step-wise, or only when re-configuration is complete.

Figure 8:
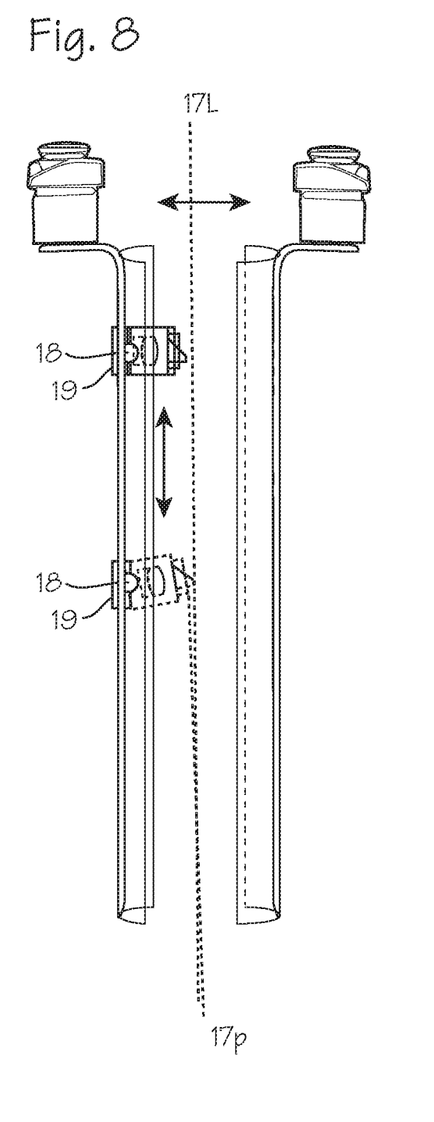
FIG. 8 shows the retractor system with a camera slidably mounted on a retractor blade.

FIG. 8 shows the retractor system with a camera slidably mounted on a retractor blade. With the camera components sized appropriately, the camera assembly 11 is slidably mounted on the retractor blade through the mount 19. This can be accomplished with a clip slidably secured to a long edge of a blade, or with a bolt or braking mechanism secured to the camera assembly and a corresponding channel in a blade, such that the bolt and camera assembly are slidable along the channel. The camera and bolt can be secured in the channel with a friction fit or detents or any other mechanism that allows a surgeon to manually slide the camera with minimal force yet maintain the position of the camera once set by the surgeon. The camera is preferably rotatably fixed to the channel, through a hinge or flex hinge, so that it may be rotated or tilted toward the center of the surgical field as the camera is moved proximally and distally along the blade, or as the blades are opened or splayed. Where the camera is quite small relative to the retractor opening, the camera assembly can be provided without a prism or reflector, and the imaging sensor viewing axis can be aimed toward the center of surgical field, and the camera can be rotated as describe above to keep the imaging sensor viewing axis intersecting the central longitudinal axis (as described above for keeping the prism viewing axis intersecting the central longitudinal axis) near the distal end of the system.

As an alternative to slidably mounting the camera to a blade, the camera assembly can include an optical pipe or fiber bundle disposed above or below the distal face of the prism (such that that distal-most optical surface is displaced distally from the imaging sensor), and the entire assembly can be translated distally or proximally along a blade. A prism may be used both at the distal end of the optical pipe to establish an optical pathway from the center of surgical field to the light pipe, and at the proximal end of the optical pipe to turn light from the optical pipe toward the imaging sensor. In each case, the camera assembly, in particular the distal most optical element (the prism, the tip of the fiber bundle, or a lens at the tip of the fiber bundle) can be translated longitudinally within the surgical opening. A light source can be added to the camera assembly, or to the inner surface of a blade. The camera assembly is preferably electrically isolated from the blades (if the blades are metallic).

Figure 9:
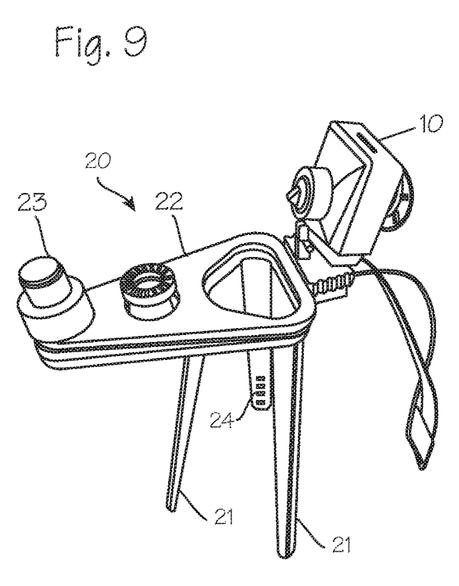
FIGS. 9 and 10 illustrate an embodiments of the retractor system.

FIG. 9 illustrates an embodiment of the retractor system 20. This system includes three blades 21 joined to a frame 22 of fixed proportions through flex hinges. The camera is mounted to the frame via a hinge (a crescent hinge, for example). The frame is fitted with a post 23 which may be secured to a mounting arm, which in turn may be fixed to an operating table used to support the patient during surgery. A number of LED's 24 are inset in the interior surface of the blades, near the distal end of the blades, to illuminate the surgical field. FIG. 10 illustrates another embodiment of the retractor system 25, with a camera retrofitted on a plier-type retractor system. This system includes three blades 21 joined to jaws 26 of an expandable frame, with the camera mounted on the frame near the distal end of one of the blades. In each case, the camera may be mounted to the frame via a hinge such that, as the jaws are opened to enlarge the retractor opening, the camera may be rotated or tilted to direct the viewing axis toward the desired area of the surgical field at the distal end of the blades.

In use, the cannula blades are positioned in a closed relationship, as close together as the frame will allow, inserted into a surgical opening in the body of a patient, and then gently pulled open to retract tissue outside the blade and enlarge the surgical opening. This will provide access to tissue deep within the body. In a lateral interbody fusion procedure, the pathway and corresponding retractor blades are quite long (20 centimeters or so), and it may be quite difficult to see tissue at or beyond the distal end of the retractor. The camera is used to obtain an image of the surgical field, to be displayed on a display screen visible to the surgeon, so that the surgeon may insert tools through the surgical opening, going through the surgical channel held open by the retractor blades, and manipulate the tools while viewing the surgical field (and at least a portion of the surgical channel) and tools on the display screen. The surgeon may tilt the camera, or slide the camera along a blade, as desired to obtain a desired field of view.

The camera assembly and mounting structures can be provided in configurations specific to particular retractors, or provided in configuration which can fit many retractors of various configurations. For example, the camera assembly may be fixed to an adjustable clamp or spring clip suitable to attachment to the frame, arm, jaw, or blade of various configurations.

FIGS. 11, 12, 13 and 14 illustrate systems comprising a camera assembly configured for attachment to a bladed retractor, with a mount for adjustably mounting the camera assembly over the surgical opening maintained by the retractor blades. In this system shown in FIG. 11, the retractor comprises the frame 5 including the ratcheted frame members 10 and arms 7 mounted on the ratcheted frame members 10, and the blades 4 which establish the surgical opening 9. The camera assembly 11 is secured to the retractor system through an articulating camera boom 31, which comprises boom arms necessary to suspend the camera over the surgical opening 9, with all the components of the camera assembly proximate the proximal end of the retractor blades, with the distal-most optical component of the camera assembly (such as the distal face of the prism or the distal surface of an objective lens) proximate the proximal end of the retractor blades, and preferably proximal to the proximal end of the retractor blades (and, preferably, outside the body of the patient), so that the entirety of the camera assembly is located outside the lumen established by the retractor blades and bounded by the distal and proximal ends of the retractor blades. In this embodiment, the articulating camera boom comprises a clamp 32 configured for releasable attachment to the frame arm 7, a first boom arm 33 extending away from the ratcheted frame member and beyond the blades (relative to the ratcheted frame member), and a second boom arm 34 extending inwardly from the first boom arm 33 to a position beyond the tips of the frame arms 7. The clamp may be slidably mounted to the frame arm, or the first boom arm 33 may be slidably connected to the clamp, so that the first boom arm 33 may be translated along a first axis of the retractor. The second boom arm 34 may be slidably mounted to the first boom arm 33, so that second boom arm 34 may be translated along a second axis of the retractor. The second boom arm 34 may also be rotatably mounted to the first boom arm 33, or the first boom arm may be rotatably mounted on the clamp. The camera assembly is mounted to the second boom arm 34, with the viewing axis aligned to the surgical opening. The camera is rotatable, relative to the first and second boom arms, about the long axis of the second boom arm 34, so that the viewing axis maybe tilted as necessary to point toward the surgical workspace at the distal end of the blades. The camera assembly may be rotatably fixed to the second boom arm 34 through a post 35 rotationally fixed to the camera housing but rotatably fixed to the second boom arm 34 (the post may fit within a bore of the second boom arm 34, or it may be formed as a turret the fits over a cylindrical portion of the second boom arm 34), or the second boom arm 34 may be rotatably fixed to the first boom arm 33. The second boom arm may also be rotatably mounted to the first boom arm, such that it is rotatable about its long axis, in which case the camera may be rotationally fixed to the second boom arm. Also, the camera assembly may be translatable, toward and away from the first boom arm 33 (while rotatably held within the second boom arm 34, to position the viewing axis near the center line C of the retractor frame arms and blades as they expand. To provide for this translation, the camera may be slidably secured to the second boom arm 34 through the post, which is, in addition to being rotatable relative to the second boom arm 34, slidably fixed within a bore 36 of the second boom arm 34. The boom arms may also be rotatably joined, to that the boom arms themselves may be rotated at a hinge point connecting the boom arms.

Figure 11:
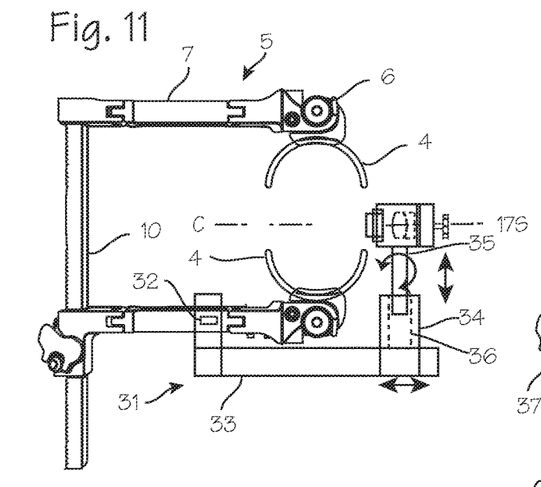
FIGS. 11, 12, 13 and 14 illustrate systems comprising a camera assembly configured for attachment to a bladed retractor, with a mount for adjustably mounting the camera over the surgical opening maintained by the retractor blades.
Figure 12:
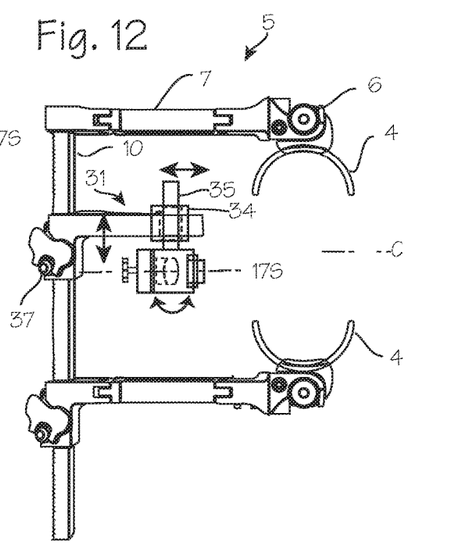
Figure 13:
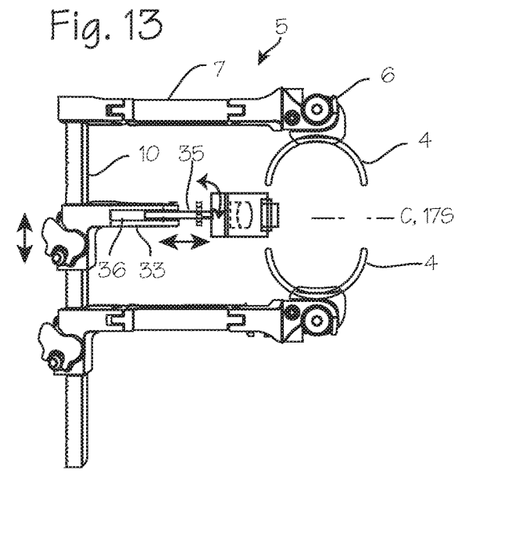

The configuration illustrated in FIG. 11 provides for positioning the camera assembly on a variety of existing bladed retractor systems in an obtrusive position, with the blades disposed between the camera assembly and the retractor frame member 10, and the specific construction can be varied as needed to fit various retractor systems or to place the camera in different positions relative to the retractor frame components. One such variation is shown in FIG. 12, which uses the same configuration of the camera assembly 11 and the post 35 orthogonally fixed to the camera assembly, with the long axis of the post disposed perpendicular to the sensing axis and/or the viewing axis, and the first boom arm 33 attached to the retractor frame member 10, between the frame arms 7. Another variation is shown in FIG. 13, in which the camera frame 31 consists of a single boom arm 33, slidably or translatably secured to the ratcheted frame member 10 with a toggle clamp 37, and the camera assembly is slidably mounted to the single boom arm so that it may be translated toward and away from the center of the surgical opening. The camera assembly may also be rotatable about the long axis of the boom arm. In this embodiment, the post 35 is disposed on the camera assembly in parallel relationship with the sensor viewing axis (which, in this embodiment, is perpendicular to the viewing axis of the camera assembly.)

Figure 14:
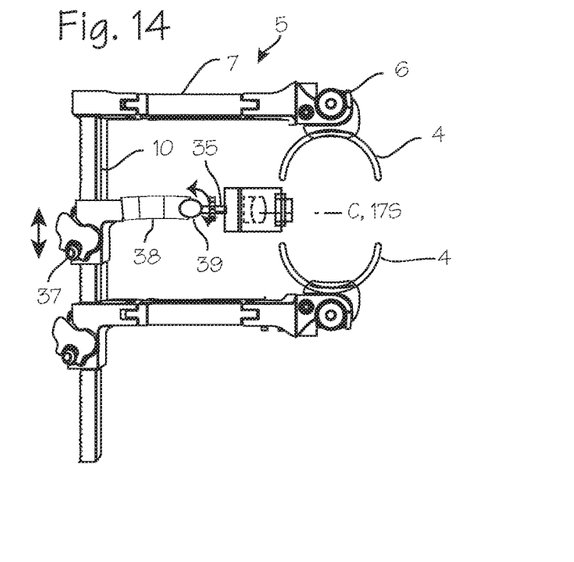

FIG. 14 illustrates a system in which the camera assembly 11 is secured to the retractor frame through a flexible and malleable member, such as flex arm (also referred to as a gooseneck or a snake clamp) 38. The flexible and malleable member may be fixed to the retractor 5 at any point, and is illustrated secured to the ratcheted frame member 10. A ball joint 39 or hinge can be used to secure the camera assembly to the flexible and malleable member. In this embodiment, the camera assembly can be disposed about the surgical opening and proximal retractor opening, with its viewing axis aimed at the surgical surgical channel or workspace, by manipulating the flex arm (and the ball joint, if it is provided).

Figure 15:
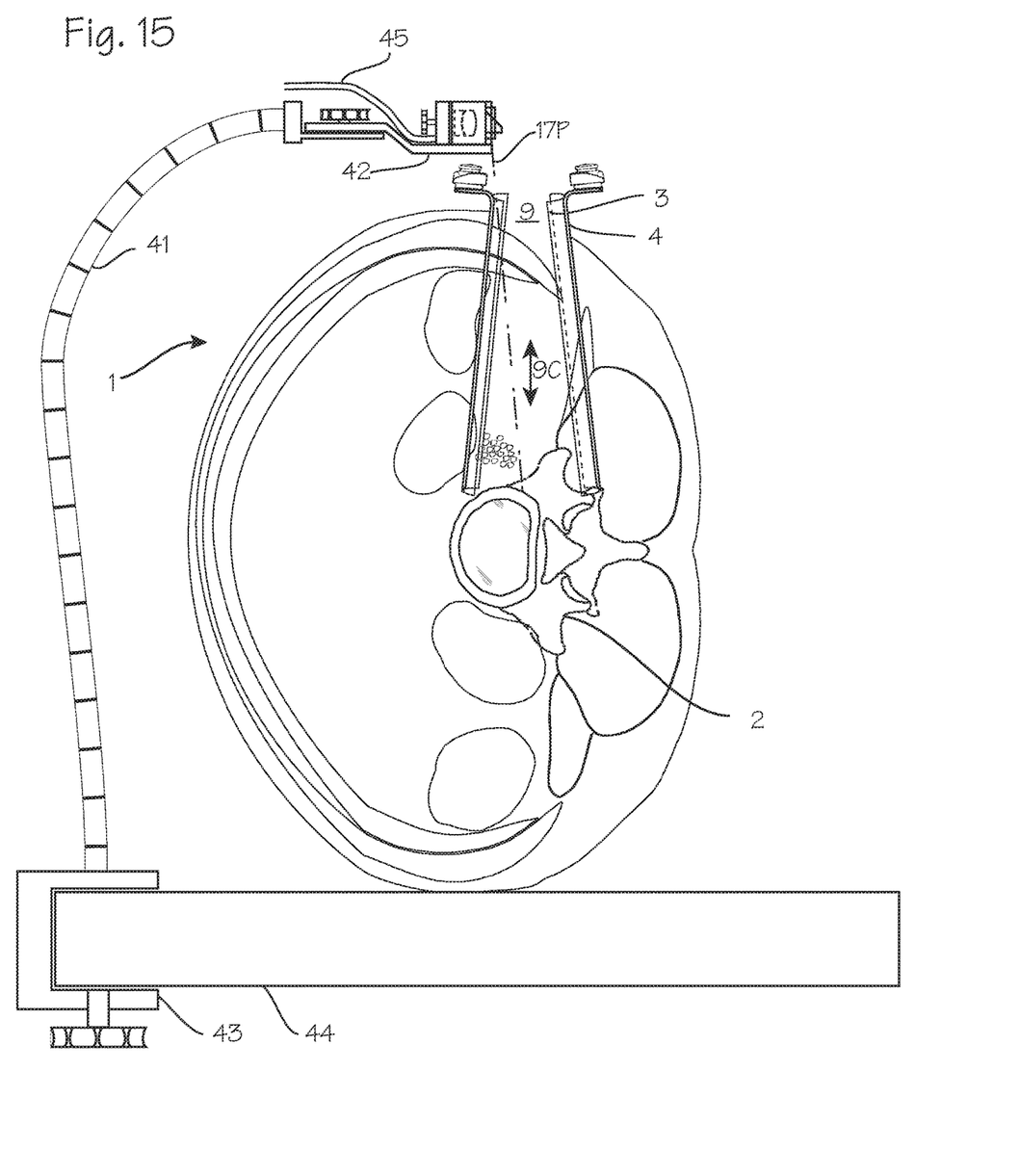
FIG. 15 illustrates a system comprising the camera assembly mounted on a table-fixed flex arm, to be used in conjunction with a bladed retractor.

FIG. 15 illustrates a system comprising the camera assembly mounted on a table-fixed flex arm, to be used in conjunction with a bladed retractor, to visualize a surgical channel established by the retractor blades or the surgical field at or near the distal end of the retractor blades. This system includes the camera assembly 11 mounted to the tip of table-fixed flex arm 41. A mounting tab 42 is fixed to the camera (the camera may be rotatable upon the tab upper surface, or rotatable relative to the long axis or transverse axis of the mounting tab) at one end, and fixed to the end of the flex arm at the other end. The flex arm includes a clamp 43 at one end for secure attachment to an operating table 44 or other structure fixed relative to the patient during surgery, and a second clamp for secure attachment of the camera assembly at the other end. A communication cable 45 used to connect the camera to a display system and a power supply can run along the flex arm. With the flex arm secured to the operating table, and the retractor installed in a surgical opening of the patient to establish the surgical channel 9C, a surgeon may position the camera over the surgical opening established by the retractor, with the prism viewing axis 17P pointed that the surgical field at the distal end of the retractor blades, to obtain images of the surgical field. The camera assembly, including the prism and the distal surface of the prism, are preferably held away from the body, proximal to (superficial to, or away from the body relative to) the surgical opening 9 and outside the surgical channel 9C. This system in intended for use in conjunction with a retractor disposed within a surgical opening of a patient, but may be used with any surgical opening with or without a retractor in the surgical opening.

The retractor systems described above can be used to approach various structures in the body, including the lumbar spine as described above, the thoracic spine, the cervical spine through, for example, an anterior approach, and various other deep tissues.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A retractor system comprising:

a retractor frame and a plurality of retractor blades characterized by a distal end and a proximal end, said retractor blades secured to the frame at their respective proximal ends, said frame operable to move the blades toward a first closely-spaced configuration and toward a second widely-spaced configuration, said retractor blades defining a central longitudinal axis and a proximal retractor opening near the proximal end of the blades, and a distal retractor opening proximate the distal ends of the retractor blades, and a surgical channel extending from said proximal retractor opening and said distal retractor opening;

a camera assembly characterized by a viewing axis and a distal optical element; and an articulated camera boom connecting the camera assembly to the retractor frame, said articulated camera boom comprising a clamp for releasably attaching the camera boom to the retractor frame, at least a first boom arm and a second boom arm, with the camera assembly rotatably mounted on the retractor system through a rotatable connection between one of second boom arm to the first boom arm or the camera assembly to the second boom arm to align the viewing axis such that the viewing axis intersects the central longitudinal axis near the distal retractor opening for the first closely-spaced configuration.

2. The retractor system of claim 1 wherein:

the clamp is slidably mounted on the retractor frame.

* * * * *